(12) United States Patent
Le-Khac

(10) Patent No.: US 7,288,237 B2
(45) Date of Patent: Oct. 30, 2007

(54) EPOXIDATION CATALYST

(75) Inventor: Bi Le-Khac, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 166 days.

(21) Appl. No.: 11/281,001

(22) Filed: Nov. 17, 2005

(65) Prior Publication Data

US 2007/0112208 A1    May 17, 2007

(51) Int. Cl.
  *C01B 33/20* (2006.01)
  *C07D 301/12* (2006.01)
  *B01J 29/89* (2006.01)

(52) U.S. Cl. .............. 423/326; 423/713; 423/DIG. 21; 502/242; 549/531

(58) Field of Classification Search ................ 423/713, 423/DIG. 21, 326; 502/242; 549/531
See application file for complete search history.

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,833,260 A | 5/1989 | Neri et al. | 549/531 |
| 5,254,746 A * | 10/1993 | Costantini et al. | 568/626 |
| 5,859,265 A | 1/1999 | Müller et al. | 549/531 |
| 5,885,546 A * | 3/1999 | Kumar et al. | 423/703 |
| 6,464,957 B1 * | 10/2002 | Kuznicki et al. | 423/713 |
| 6,669,924 B1 * | 12/2003 | Kaliaguine et al. | 423/702 |

FOREIGN PATENT DOCUMENTS

| | | |
|---|---|---|
| BE | 1001038 A7 | 6/1989 |
| JP | 4-352771 | 12/1992 |
| WO | WO98/00413 | 1/1998 |

* cited by examiner

*Primary Examiner*—David Sample
(74) *Attorney, Agent, or Firm*—Kevin M. Carroll

(57) ABSTRACT

Titanium or vanadium zeolite catalysts are prepared by reacting a titanium or vanadium compound, a silicon source, a templating agent, a hydrocarbon, and a surfactant at a temperature and for a time sufficient to form a molecular sieve. The catalyst is useful in olefin epoxidation with hydrogen peroxide.

25 Claims, No Drawings

EPOXIDATION CATALYST

FIELD OF THE INVENTION

This invention relates to a process for producing a titanium or vanadium zeolite catalyst and its use in olefin epoxidation with hydrogen peroxide.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and organic hydroperoxides, another oxidizing agent useful for the preparation of epoxides is hydrogen peroxide. U.S. Pat. No. 4,833,260, for example, discloses the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

Titanosilicates and vanadosilicates are typically produced by a hydrothermal crystallization procedure, for example, as described in U.S. Pat. Nos. 4,410,501 and 4,833,260. Lee and Shantz, in *Chem. Comm.*, 2004, 680-681, disclose a method to modify the particle size and morphology of silicate-1 using microemulsions, such as a water/oil/surfactant mixture in the synthesis of silicate-1. However, Lee and Shantz do not disclose then synthesis of titanosilicates nor olefin epoxidation processes.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is process for producing a titanium or vanadium zeolite catalyst. The process comprises reacting a titanium or vanadium compound, a silicon source, a templating agent, a hydrocarbon, and a surfactant at a temperature and for a time sufficient to form a molecular sieve. The catalyst is active in olefin epoxidation with hydrogen peroxide, and demonstrates higher productivity and selectivity to epoxide compared to zeolites produced without hydrocarbon and surfactant additives.

DETAILED DESCRIPTION OF THE INVENTION

The process of the invention is used to produce titanium or vanadium zeolites. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,833,260.

The process of the invention comprises reacting a titanium or vanadium compound, a silicon source, a templating agent, a hydrocarbon and a surfactant at a temperature and for a time sufficient to form a molecular sieve. The process is typically performed in the presence of water. Other solvents such as alcohols may also be present. Alcohols such as isopropyl, ethyl and methyl alcohol are preferred, and isopropyl alcohol is especially preferred.

Although the process of the invention is not limited by choice of a particular titanium or vanadium compound, suitable titanium or vanadium compounds useful in the invention include, but are not limited to, titanium or vanadium alkoxides and titanium or vanadium halides. Preferred titanium alkoxides are titanium tetraisopropoxide, titanium tetraethoxide and titanium tetrabutoxide. Titanium tetraethoxide is especially preferred. Preferred titanium halides include titanium trichloride and titanium tetrachloride.

Suitable silicon sources include, but are not limited to, colloidal silica, fumed silica and silicon alkoxides. Preferred silicon alkoxides are tetraethylorthosilicate, tetramethylorthosilicate, and the like. Tetraethylorthosilicate is especially preferred.

The templating agent is typically a tetraalkylammonium hydroxide, tetraalkylammonium halide, tetraalkylammonium nitrate, tetraalkylammonium acetate, and the like. Tetraalkylammonium hydroxides and tetraalkylammonium halides, such as tetrapropylammonium hydroxide and tetrapropylammonium bromide, are preferred. Tetrapropylammonium hydroxide is especially preferred.

The hydrocarbon is typically a non-oxygenated hydrocarbon. Preferred non-oxygenated hydrocarbons are those that do not contain any oxygen atoms and are liquid at ambient temperatures. Particularly preferred classes of hydrocarbons include $C_5$-$C_{12}$ aliphatic hydrocarbons (straight chain, branched, or cyclic), $C_6$-$C_{12}$ aromatic hydrocarbons (including alkyl-substituted aromatic hydrocarbons), $C_1$-$C_{10}$ halogenated aliphatic hydrocarbons, $C_6$-$C_{10}$ halogenated aromatic hydrocarbons, and mixtures thereof. Examples of suitable hydrocarbon solvents include n-hexane, n-heptane, cyclopentane, methyl pentanes, cyclohexane, methyl cyclohexane, dimethyl hexanes, toluene, xylenes, methylene chloride, chloroform, dichloroethanes, chlorobenzene, benzyl chloride, and the like.

The surfactant may be any suitable nonionic, ionic, cationic or amphoteric surfactant. Preferably, the surfactant is a nonionic surfactant, such as alkoxylated adducts of alcohols, diols, or polyols. Such surfactants typically comprise the condensation product of one mole of alcohol (or diol or polyol) with 1 to about 50, preferably 1 to about 20, more preferably 2 to about 10, moles of ethylene oxide (EO) or propylene oxide (PO). Suitable surfactants include the alkylene oxide adducts of acetylenic diols such as the Surfynol® products from Air Products, which comprise the ethoxylated adducts of 2,4,7,9-tetramethyl-5-decyne-4, 7-diol. Suitable surfactants also include polyoxyethylene polyoxypropylene alkyl ether, polyoxyethylene alkyl ether, polyoxyethylene alkylallyl ether, polyoxyethylene alkylaryl ether, polyoxyethylene nonylphenyl ether, and polyoxyethylene octylphenyl ether. Of these, polyoxyethylene alkyl ethers and polyoxyethylene alkylaryl ethers are most preferred. Particularly preferred are polyoxethylene nonylphenyl ether, polyoxethylene octylphenyl ether, and the like.

Generally, the hydrothermal process used to prepare titanium or vanadium zeolites involves forming a reaction mixture wherein the molar ratios of additives (as defined in terms of moles of templating agent, moles of $SiO_2$ and moles of $TiO_2$ or $VO_{2.5}$) preferably comprise the following molar ratios: $TiO_2(VO_{2.5}):SiO_2=0.5$-$5:100$; and templating agent:$SiO_2=10$-$50:100$. The water:$SiO_2$ molar ratio is preferably from about 1000-5000:100 and the solvent:$SiO_2$ molar ratio may be in the range of 0-500:100. The titanium or vanadium source, silicon source, templating agent, and water (and solvent, if added) combined together form a clear gel mother liqueur. The weight ratio of hydrocarbon:clear gel is preferably from about 0.5 to about 20. The weight ratio of surfactant:clear gel is preferably from about 0.001 to about 0.25.

The reaction mixture may be prepared by mixing the desired sources of titanium or vanadium, silicon, and templating agent with the hydrocarbon and surfactant to form the reaction mixture. After forming the reaction mixture, it is also typically necessary that the mixture have a pH of about 9 to about 13. The basicity of the mixture is controlled by the amount of templating agent (if it is in the hydroxide form) which is added and/or the use of other basic compounds. If another basic compound is used, the basic compound is preferably an orgasmic base that is free of alkali metals, alkaline earth metals, and the like. The addition of other basic compounds may be needed if the templating agent is added as a salt, e.g., halide or nitrate. Examples of these basic compounds include ammonium hydroxide, quaternary ammonium hydroxides and amines. Specific examples include tetraethylammonium hydroxide, tetrabutylammonium hydroxide, n-butylamine, and tripropylamine.

The order of addition of the titanium or vanadium compound, silicon source, templating agent, hydrocarbon, and surfactant to form the reaction mixture is not considered critical to the invention. For instance, these compounds can be added all at once to form the reaction mixture. Alternatively, the reaction mixture may be prepared by first mixing the desired sources of titanium or vanadium, silicon, and templating agent to give an initial reaction mixture. If necessary, the initial reaction mixture may be adjusted to a pH of about 9 to about 13 as described above. Hydrocarbon and surfactant are then added to the initial reaction mixture to form the reaction mixture.

After the reaction mixture is formed, it is reacted at a temperature and a time sufficient to form a molecular sieve. Typically, the reaction mixture is heated at a temperature of about 100° C. to about 250° C. for a period greater than about 0.25 hours (preferably less than about 96 hours) in a sealed vessel under autogenous pressure. Preferably, the reaction mixture is heated at a temperature range from about 125° C. to about 200° C., most preferably from about 150° C. to about 180° C. The reaction may be carried out in a batch, continuous, or semi-continuous manner using any appropriate type of reaction vessel or apparatus such as a stirred vessel or CSTR reactor. In a continuous or semi-continuous process, it is preferable to first form an initial reaction mixture prepared by first mixing the desired sources of titanium or vanadium, silicon, and templating agent, and preferably adjusting to a pH of about 9 to about 13. This initial reaction mixture and a separate mixture containing the hydrocarbon and surfactant are then added simultaneously to the continuous or semi-continuous reaction vessel, and titanium or vanadium zeolite is continuously removed from the reaction vessel.

After the reaction is complete, the titanium or vanadium zeolite is recovered. Suitable zeolite recovery methods include filtration and washing (typically with deionized water), rotary evaporation, centrifugation, and the like. The titanium or vanadium zeolite may be dried at a temperature greater than about 20° C., preferably from about 50° C. to about 200° C.

As synthesized, the titanium or vanadium zeolites of this invention will contain some of the templating agent or the additional basic compounds in the pores. Any suitable method to remove the templating agent may be employed. The template removal may be performed by a high temperature heating in the presence of an inert gas or an oxygen-containing gas stream. Alternatively, the template may be removed by contacting the zeolite with ozone at a temperature of from 20° C. to about 800° C. The zeolite may also be contacted with an oxidant such as hydrogen peroxide (or hydrogen and oxygen to form hydrogen peroxide in situ) or peracids to remove the templating agent. The zeolite may also be contacted with an enzyme, or may be exposed to an energy source such as microwaves or light in order to decompose the templating agent.

Preferably, the titanium or vanadium zeolite is heated at temperatures greater than 250° C. to remove the templating agent. Temperatures of from about 275° C. to about 800° C. are preferred, and most preferably from about 300° C. to about 600° C. The high temperature heating may be conducted in inert atmosphere which is substantially free of oxygen, such as nitrogen, argon, neon, helium or the like or mixture thereof. By "substantially free of oxygen", it is meant that the inert atmosphere contains less than 10,000 ppm mole oxygen, preferably less than 2000 ppm. Also, the heating may be conducted in an oxygen-containing atmosphere, such as air or a mixture of oxygen and an inert gas. Alternatively, the titanium or vanadium zeolite may also be heated in the presence of an inert gas such as nitrogen prior to heating in an oxygen-containing atmosphere. The heating process may be conducted such that the gas stream (inert, oxygen-containing, or both) is passed over the titanium or vanadium zeolite. Alternatively, the heating may be performed in a static manner. The zeolite could also be agitated or stirred while being contacted with the gas stream.

If the as-synthesized titanium or vanadium zeolite is produced in the form of a powder, it may be spray dried, pelletized or extruded prior to the heating step. If spray dried, pelletized or extruded, the noble metal-containing titanium or vanadium zeolite may additionally comprise a binder or the like and may be molded, spray dried, shaped or extruded into any desired form prior the heating step.

The titanium zeolite preferably is of the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 may also be formed during the synthesis.

The epoxidation process of the invention comprises contacting an olefin and hydrogen peroxide in the presence of the titanium or vanadium zeolite catalyst. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The hydrogen peroxide may be generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical hydrogen peroxide concentrations range from 0.1 to 90 weight percent hydrogen peroxide in water, preferably 1 to 5 weight percent.

The amount of hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The hydrogen peroxide may also be generated in situ by the reaction of hydrogen and oxygen in the presence of a noble metal catalyst. Although any sources of oxygen and hydrogen are suitable, molecular oxygen and molecular hydrogen are preferred.

While any noble metal catalyst can be utilized (i.e., gold, silver, platinum, palladium, iridium, ruthenium, osmium metal catalysts), either alone or in combination, palladium, platinum and gold metal catalysts are particularly desirable. Suitable noble metal catalysts include high surface area noble metals, noble metal alloys, and supported noble metal catalysts. Examples of suitable noble metal catalysts include high surface area palladium and palladium alloys. However, particularly preferred noble metal catalysts are supported noble metal catalysts comprising a noble metal and a support.

For supported noble metal catalysts, the support is preferably a porous material. Supports are well-known in the art. There are no particular restrictions on the type of support that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

Preferably, the support has a surface area in the range of about 10 to about 700 $m^2/g$, more preferably from about 50 to about 500 $m^2/g$, and most preferably from about 100 to about 400 $m^2/g$. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 μm, more preferably from about 1 to about 200 μm, and most preferably from about 10 to about 100 μm. The average pore diameter is typically in the range of about 10 to about 1000 Å, preferably about 20 to about 500 Å, and most preferably about 50 to about 350 Å.

The supported noble metal catalyst contains a noble metal. While any of the noble metals can be utilized (i.e., gold, silver, platinum, palladium, iridium, ruthenium, osmium), either alone or in combination, palladium, platinum and gold are particularly desirable. Typically, the amount of noble metal present in the supported catalyst will be in the range of from 0.001 to 20 weight percent, preferably 0.005 to 10 weight percent, and particularly 0.01 to 5 weight percent. The manner in which the noble metal is incorporated into the catalyst is not considered to be particularly critical. For example, the noble metal may be supported by impregnation, adsorption, precipitation, or the like. Alternatively, the noble metal can be incorporated by ion-exchange with, for example, tetraammine palladium dichloride.

There are no particular restrictions regarding the choice of noble metal compound or complex used as the source of the noble metal in the supported catalyst. For example, suitable compounds include the nitrates, sulfates, halides (e.g., chlorides, bromides), carboxylates (e.g. acetate), and amine complexes of noble metals.

In one preferred embodiment of the invention, the epoxidation of olefin, hydrogen and oxygen is carried out in the presence of a noble metal-containing titanium or vanadium zeolite which comprises a noble metal and the titanium or vanadium zeolite of the invention. In this embodiment, the noble metal is incorporated into the titanium or vanadium zeolite by the methods described above.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical) phase, it is advantageous to work at a pressure of 1-200 bars and in the presence of one or more solvents. Suitable solvents include, but are not limited to, alcohols, ketones, water, $CO_2$, or mixtures thereof. Suitable alcohols include $C_1$-$C_4$ alcohols such as methanol, ethanol, isopropanol, and tert-butanol, or mixtures thereof. If $CO_2$ is used as a solvent, the $CO_2$ may be in the supercritical state or in a high pressure/subcritical state. Fluorinated alcohols can be used. It is preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may preferably range from 3 to 12, more preferably from 4 to 10 and most preferably from 5 to 9. Suitable salts of oxyacids contain an onion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. Buffers may preferably contain a combination of more than one suitable salt. Typically, the concentration of buffer in the solvent is from about 0.0001 M to about 1 M, preferably from about 0.0005 M to about 0.3 M. The buffer useful in this invention may also include the addition of ammonia gas or ammonium hydroxide to the reaction system. For instance, one may use a pH=12-14 solution of ammonium hydroxide to balance the pH of the reaction system. More preferred buffers include alkali metal phosphate, ammonium phosphate, and ammonium hydroxide buffers.

The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0-150° C., more preferably, 20-120° C. Reaction or residence times of from about 1 minute to 48 hours, more preferably 1 minute to 8 hours will typically be appropriate. It is advantageous to work at a pressure of 1 to 200 atmospheres, although the reaction can also be performed at atmospheric pressure.

The following examples merely illustrate the invention. Those skilled in the art will recognize many variations that are within the spirit of the invention and scope of the claims.

COMPARATIVE EXAMPLE 1

Preparation of TS-1 Catalyst Without Hydrocarbon and Surfactant

TS-1 may be prepared according to any standard procedure. A typical procedure follows:

A dry 2-gallon stainless steel autoclave, with a nitrogen purge, agitator, thermocouple, addition ports and valves, and an over-pressure relief disc, is set in an ice bath to cool it to 0° C. and purged under nitrogen feed. Tetraethyl orthosilicate (TEOS, 1978.4 g) is charged to the vessel and the agitator is run at 1000 rpm. Tetraethyl orthotitanate (TEOT, 60.4 g) is then added over 30 to 60 minutes, with vigorous mixing, while maintaining the ice bath cooling. A 15 wt. % aqueous solution of tetrapropyl ammonium hydroxide (TPAOH, prepared by adding 1447.1 g of 40 wt. % aqueous TPAOH and 2413.7 g of deionized water) is then added to the vessel over 2 hours, with continued cooling. After TPAOH addition, the ice bath is removed and stirring is continued until the mixture reaches room temperature. A clear gel mother liqueur is obtained (Clear Gel 1).

A portion of Clear Gel 1 is stirred at 200 rpm and heated to 170° C. over 5 hours ramping, held at 170° C. for 24 hours, and then cooled. The TS-1 product crystals are filtered, washed three times with deionized water, dried under vacuum at 55° C. for 2 hours, and oven calcined in air by heating from 20 to 110° C. at 10° C./min and holding at 110° C. for 2 hours, then heating to 550° C. at 2° C./min and holding at 550° C. for 4 hours to produce Comparative Catalyst 1.

EXAMPLE 2

Preparation of TS-1 Catalyst with Hydrocarbon and Surfactant

Clear Gel 1 (100 g, Comparative Example 1), Igepal® CO-720 (20 g, polyoxyethylene(12)nonylphenyl ether, product of Aldrich), and heptane (140 g) are charged into a 450-mL Parr reactor. After the reactor is closed and flushed with nitrogen, the reactor is heated to 180° C. over 30 minute ramping, and held at 180° C. for 3.5 hours with mixing at 800 rpm. After cooling the reactor to room temperature, the solid is isolated by centrifugation, washed twice with distilled water, and dried in a vacuum oven at 60-70° C. to constant weight (9.22 g). A portion of the solid (4.75 g) is treated with nitrogen at 550° C. for 2 hours, then calcined in air at 110° C. for 2 hours, followed by 550° C. for 4 hours to produce Catalyst 2 (4.09 g).

EXAMPLE 3

TS-1 Catalyst Preparation with Hydrocarbon and Surfactant Using a Semi-Continuous Process Heptane (140 g) and Igepal CO-720 (20 g) are charged into a 450-mL Parr reactor. After the reactor is closed and flushed with nitrogen, the reactor is heated to 180° C. over 30 minutes, and held at 180° C. with mixing at 800 rpm. Clear gel 1 (100 g, Comparative Example 1) is then added continuously to the reactor for 2 hours, and the reaction is continued at 180° C. for another 3 hours. After cooling the reactor to room temperature, the solid is isolated by centrifugation, washed twice with distilled water, and dried in a vacuum oven at 60-70° C. to constant weight (8 g). The solid is treated with nitrogen at 550° C. for 2 hours, then calcined in air at 110° C. for 2 hours, followed by 550° C. for 4 hours to produce Catalyst 3 (7.08 g).

EXAMPLE 4

Epoxidation of Propylene

A 100-mL Parr reactor is charged with a 70:25:5 wt. % solution of methanol/water/hydrogen peroxide (40 g) and catalyst (0.15 g). The reactor is sealed and charged with propylene (23 to 25 g). The magnetically stirred reaction mixture is heated at 50° C. for 30 minutes at a reactor pressure about 280 psig, and is then cooled to 10° C. The liquid and gas phases are analyzed by gas chromatography. Propylene oxide and equivalents ("POE") are produced during the reaction. POE produced include propylene oxide ("PO") and the ring-opened products propylene glycol and glycol ethers. Results appear in Table 1.

Example 4A uses Comparative Catalyst 1. Example 4B uses Catalyst 2. Example 4C uses Catalyst 3.

The results show both higher productivity and selectivity for olefin epoxidation reactions using titanium zeolites produced in the presence of a hydrocarbon and a surfactant.

TABLE 1

EPOXIDATION RESULTS WITH HYDROGEN PEROXIDE

| Example | H$_2$O$_2$ Conversion (%) | PO produced (mmol) | POE produced (mmol) | PO/H$_2$O$_2$ Selectivity | PO/POE Selectivity (%)[1] |
|---|---|---|---|---|---|
| 4A * | 66.7 | 31.7 | 35.9 | 80.6 | 88.2 |
| 4B | 82 | 45.9 | 46.5 | 95.1 | 98.7 |
| 4C | 67.7 | 40.4 | 40.7 | 97 | 99.4 |

* Comparative Example
[1] PO/POE Selectivity = moles PO/(moles PO + moles glycols + moles glycol ethers) * 100.

I claim:

1. A process for producing a titanium or vanadium zeolite comprising reacting a titanium or vanadium compound, a silicon source, a templating agent, a hydrocarbon and a surfactant at a temperature and for a time sufficient to form a molecular sieve.

2. The process of claim 1 wherein the titanium compound is selected from the group consisting of titanium halides, titanium alkoxides, and mixtures thereof.

3. The process of claim 1 wherein the silicon source is selected from the group consisting of colloidal silica, fumed silica, silicon alkoxides, and mixtures thereof.

4. The process of claim 1 wherein the templating agent is selected from the group consisting of tetraalkylammonium hydroxide, tetraalkylammonium halides, and mixtures thereof.

5. The process of claim 1 wherein the hydrocarbon is selected from the group consisting of C$_5$-C$_{12}$ aliphatic hydrocarbons, C$_6$-C$_{12}$ aromatic hydrocarbons, C$_1$-C$_{10}$ halogenated aliphatic hydrocarbons, C$_6$-C$_{10}$ halogenated aromatic hydrocarbons, and mixtures thereof.

6. The process of claim 1 wherein the surfactant is selected from the group consisting of polyoxyethylene polyoxypropylene alkyl ether, polyoxyethylene alkyl ether, polyoxyethylene alkylallyl ether, polyoxyethylene alkylaryl ether, polyoxyethylene nonylphenyl ether, polyoxyethylene octylphenyl ether, alkylene oxide adducts of acetylenic diols, and mixtures thereof.

7. A process for producing an epoxide comprising reacting an olefin and hydrogen peroxide in the presence of a titanium or vanadium zeolite, wherein the titanium or vanadium zeolite is produced by reacting a titanium or vanadium compound, a silicon source, a templating agent, a hydrocarbon, and a surfactant at a temperature and for a time sufficient to form a molecular sieve.

8. The process of claim 7 wherein the titanium compound is selected from the group consisting of titanium halides, titanium alkoxides, and mixtures thereof.

9. The process of claim 7 wherein the silicon source is selected from the group consisting of colloidal silica, fumed silica, silicon alkoxides, and mixtures thereof.

10. The process of claim 7 wherein the templating agent is selected from the group consisting of tetraalkylammonium hydroxide, tetraalkylammonium halides, and mixtures thereof.

11. The process of claim 7 wherein the hydrocarbon is selected from the group consisting of C$_5$-C$_{12}$ aliphatic hydrocarbons, C$_6$-C$_{12}$ aromatic hydrocarbons, C$_1$-C$_{10}$ halogenated aliphatic hydrocarbons, C$_6$-C$_{10}$ halogenated aromatic hydrocarbons, and mixtures thereof.

12. The process of claim 7 wherein the surfactant is selected from the group consisting of polyoxyethylene polyoxypropylene alkyl ether, polyoxyethylene alkyl ether, polyoxyethylene alkylallyl ether, polyoxyethylene alkylaryl ether, polyoxyethylene nonylphenyl ether, polyoxyethylene octylphenyl ether, alkylene oxide adducts of acetylenic diols, and mixtures thereof.

13. The process of claim 7 wherein the titanium or vanadium zeolite is titanium silicalite.

14. The process of claim 7 wherein the olefin is a C$_2$-C$_6$ olefin.

15. The process of claim 7 wherein the olefin is propylene.

16. The process of claim 7 wherein reaction of olefin and hydrogen peroxide is performed in a solvent selected from the group consisting of water, C$_1$-C$_4$ alcohols, CO$_2$, and mixtures thereof.

17. The process of claim 7 wherein the hydrogen peroxide is formed by the in situ reaction of hydrogen and oxygen in the presence of a noble metal catalyst.

18. The process of claim 17 wherein the noble metal catalyst comprises a noble metal and a support.

19. The process of claim 18 wherein the noble metal is selected from the group consisting of palladium, platinum, and gold.

20. The process of claim 18 wherein the support is carbon, titania, zirconia, niobium oxides, silica, alumina, silica-alumina, tantalum oxides, molybdenum oxides, tungsten oxides, titania-silica, zirconia-silica, niobia-silica, and mixtures thereof.

21. A process for producing an epoxide comprising reacting an olefin, hydrogen and oxygen in the presence of a noble metal-containing titanium or vanadium zeolite comprising a noble metal and a titanium or vanadium zeolite, wherein the titanium or vanadium zeolite is produced by reacting a titanium or vanadium compound, a silicon source, a templating agent, a hydrocarbon, and a surfactant at a temperature and for a time sufficient to form a molecular sieve.

22. The process of claim 21 wherein the titanium or vanadium zeolite is titanium silicalite.

23. The process of claim 21 wherein the olefin is a C$_2$-C$_6$ olefin.

24. The process of claim 21 wherein the olefin is propylene.

25. The process of claim 21 wherein reaction of olefin, hydrogen and oxygen is performed in a solvent selected from the group consisting of water, C$_1$-C$_4$ alcohols, CO$_2$, and mixtures thereof.

* * * * *